United States Patent [19]

Shimamura

[11] Patent Number: 5,135,957
[45] Date of Patent: Aug. 4, 1992

[54] THERAPEUTIC AGENT FOR TINEA

[75] Inventor: Tadakatsu Shimamura, 4-4, Nishihara 1-chome, Shibuya-ku, Tokyo, Japan

[73] Assignees: Mitsui Norin Co., Ltd.; Tadakatsu Shimamura, both of Tokyo, Japan

[21] Appl. No.: 533,463

[22] Filed: Jun. 5, 1990

[30] Foreign Application Priority Data

Mar. 1, 1990 [JP] Japan ................................. 2-47205

[51] Int. Cl.$^5$ .................... A61K 31/045; A61K 35/78
[52] U.S. Cl. .................................. 514/738; 424/195.1
[58] Field of Search ..................... 424/195.1; 514/738

[56] References Cited

U.S. PATENT DOCUMENTS 4,613,672  9/1986  Hara .
4,673,530  6/1987  Hara .
4,840,966  6/1989  Hara et al. .................... 514/456
4,913,909  4/1990  Hara et al. .

OTHER PUBLICATIONS

*Japanese Journal of Bacteriology*, 45, No. 1, p. 352 (1990), with English translation thereof.

*Primary Examiner*—John W. Rollins
*Attorney, Agent, or Firm*—Frishauf, Holtz, Goodman & Woodward

[57] ABSTRACT

A method of treating a patient suffering from tinea comprising applying to an affected part of the skin of the patient an anti-tinea effective amount of at least one tea polyphenol.

15 Claims, No Drawings

THERAPEUTIC AGENT FOR TINEA

BACKGROUND OF THE INVENTION

The present invention relates to a therapeutic agent for tinea. More particularly, the present invention relates to a therapeutic agent for tinea, which comprises a tea extract as a main component.

As diseases caused by the parasitism of tinea fungus (filamentous fungus belonging to the genus *Trichophyton*), there can be mentioned tinea pedis (foot ringworm), tinea capitis (head ringworm), tinea corpis (body ringworm), tinea cruris (inguinal ringworm), tinea manis (hand ringworm), tinea unguim (nail ringworm) and tinea scrotis. These diseases are generally called "tinea", a kind of skin diseases peculiar to men. Iodine tincture, salicylic acid vaseline, tar paste, Griseofulvin ointment, ichthyol/zinc oxide oil, aqueous boric acid and other medicines are known as therapeutic agents for remedy of tinea. However, the therapeutic effects of these agents are not satisfactory, and it often happens that even if tinea is once seemingly cured, it recurs and becomes chronic. Moreover, direct external application of these agents to the affected parts involves troubles such as toxicity and skin irritation. Therefore, development of an effective therapeutic agent for tinea, which can be applied to the affected parts with safety, is eagerly desired.

SUMMARY OF THE INVENTION

The inventor searched for a substance having an intended therapeutic affect among natural products, apart from chemical synthetic products, and as the result, it was found that the target substance is contained in tea and tea polyphenols. The inventor has now completed the present invention based on this finding.

More specifically, in accordance with the present invention, there is provided a therapeutic agent for tinea, which comprises a tea extract as a main component.

DETAILED DESCRIPTION OF THE INVENTION

A principal component of the tea extract is tea polyphenol compounds, and said tea polyphenol compounds include the tea catechin compounds represented by the general formula (I) given below and the theaflavin compounds represented by the general formula (II) given below, and also thearubigin:

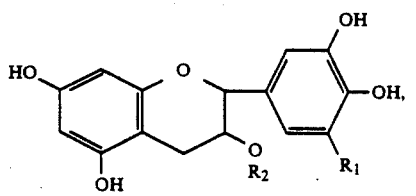
(I)

in which $R_1$ is a hydrogen atom or a hydroxy group and $R_2$ is a hydrogen atom or a 3,4,5-trihydroxy benzoyl group; and

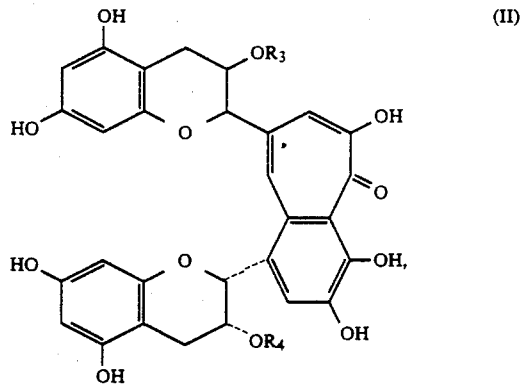
(II)

in which $R_3$ and $R_4$ are, each independently from the other, a hydrogen atom or a 3,4,5-trihydroxy benzoyl group.

Particular examples of the tea catechin compounds represented by the general formula (I) include: (−)epicatechin, which is a compound of the formula (I) with $R_1=H$ and $R_2=H$; (−)epigallocatechin, which is a compound of the formula (I) with $R_1=OH$ and $R_2=H$; (−)epicatechin gallate, which is a compound of the formula (I) with $R_1=H$ and $R_2=3,4,5$-trihydroxy benzoyl group; and (−)epigallocatechin gallate, which is a compound of the formula (I) with $R_1=OH$ and $R_2=3,4,5$-trihydroxy benzoyl group. Particular examples of the theaflavin compounds include: free theaflavin, which is a compound of the formula (II) with $R_3=H$ and $R_4=H$; theaflavin monogallate A, which is a compound of the formula (II) with $R_3=3,4,5$-trihydroxy benzoyl group and $R_4=H$; theaflavin monogallate B, which is a compound of the formula (II) with $R_3=H$ and $R_4=3,4,5$-trihydroxy benzoyl group; and theaflavin digallate, which is a compound of the formula (II) with $R_3=3,4,5$-trihydroxy benzoyl group and $R_4=3,4,5$-trihydroxy benzoyl group.

The above described tea polyphenol compounds can be prepared from tea leaves as the starting material and a method for the preparation thereof and a typical example of the product composition are described, for example, in Japanese Patent Kokai 59-219384, 60-13780 and 61-130285, etc.

When the therapeutic agent for tinea according to the present invention is used, the concentration of the tea extract as the main component can be determined according to the contents of tea polyphenols such as catechins and theaflavins. Namely, the concentration of the tea extract is determined so that the tea polyphenol content is 0.1 to 500 ppm, preferably about 2 to about 100 ppm. More specifically, an extract obtained by extracting starting tea at 5 to 0.001%, preferably 1 to 0.01%, is used. The form of the therapeutic agent for tinea includes not only a liquid but also an ointment prepared according to customary procedures.

The therapeutic agent for tinea according to the present invention has a sufficient antifungal action to tinea fungus, and since the therapeutic agent of the present invention comprises as a main component the natural product which is daily drank in considerable quantities and the safety of which is thus confirmed, the therapeutic agent is used without anxiety.

Therefore, the therapeutic agent for tinea according to the present invention has a very high practical utility.

The present invention will now be described in detail with reference to the following examples.

EXAMPLE 1

A 20% (w/v) phosphate buffer extract of commercially available black tea was prepared, and the extract was appropriately diluted and used. *Trichophyton mentagrophytes* TIMM 1188 strain and *Trichophyton rubrum* TIMM 1216 strain were used as the tinea fungus. The fungus was slant-cultured at 27° C. for 10 days, and Tween 80 (0.05%)-added physiological saline solution was added to the culture product to separate and float conidiophores. The suspension was filtered through gauze, and a fungus liquid was prepared based on the absorbance at 530 nm by using a turbidimeter (CORONA UT-11). The following tests were carried out by using this fungus liquid.

1) Antifungal Test

An agar plate containing 5% or 2.5% of the tea extract was prepared by using yeast morphology agar (supplied by Difco), and the plate was inoculated with 5 μl of the fungus liquid containing $1 \times 10^4$ to $1 \times 10^6$ of conidiophores per ml by the spot method, and culturing was conducted at 27° to 30° C. for 2 or 4 days and the evaluation was made.

As the result, it was found that the tea extract showed apparently an antifungal effect on the tinea fungus, and in the control group, sufficient growth of hyphae was observed by 4 days' culturing, while no growth of hyphae was observed at all in the tea extract-added group.

2) Fungicidal Test

Equal amounts of a twice-concentrated Sabouraud culture medium in which conidiophores were floated and a tea extract (5% or 2.5%) were mixed, and culturing was conducted. A Sabouraud agar plate was inoculated with 5 μl of the culture medium at predetermined time intervals by the spot method and the growth of the fungus was observed.

As the result, it was found that the fungicidal effect of the tea extract had a concentration dependency, but if the contact time was prolonged (48 to 72 hours), a fungicidal effect was manifested even at a low concentration.

EXAMPLE 2

In Example 1—1), an agar plate in which a predetermined amount of epigallocatechin gallate (EGCg) or theaflavin digallate (TF3) was incorporated instead of the tea extract was prepared, and 5 μl of a suspension of conidiophores ($1 \times 10^{6-7}$/ml) was inoculated on the plate by the spot method. Other procedures were the same as in Example 1. The results are shown in Table 1.

TABLE 1

| Tinea Fungus | Chemical | Amount of Chemical used (mg/ml) | | | | | | Control |
|---|---|---|---|---|---|---|---|---|
| | | 2.5 | 1.25 | 0.5 | 0.1 | 0.05 | 0.01 | |
| *Trichophyton mentagrophytes* | EGCg | − | − | + | + | + | + | + |
| | TF3 | − | − | − | + | + | + | + |
| *Trichophyton rubrum* | EGCg | − | − | + | + | + | + | + |
| | TF3 | − | − | − | + | + | + | + |

−: no growth
+: growth

What is claimed is:

1. A method of treating a patient suffering from tinea comprising applying to an affected part of the skin of the patient an anti-tinea effective amount of at least one tea polyphenol.

2. The method of treating tinea as claimed in claim 1, wherein the tea polyphenol is selected from the group consisting of (−)epicatechin, (−)epigallocatechin, (−)epicatechingallate, (−)epigallocatechingallate, free theaflavin, theaflavin monogallate A, theaflavin monogallate B and theaflavin digallate.

3. The method of treating tinea as claimed in claim 1, wherein the tea polyphenol is selected from the group consisting of catechins and theaflavins.

4. The method of treating tinea as claimed in claim 3, wherein the tea polyphenol is in a concentration of 0.1 to 500 ppm.

5. The method of treating tinea as claimed in claim 4, wherein the tea polyphenol is in a concentration of 2 to 100 ppm.

6. The method of treating tinea as claimed in claim 4, wherein the tea polyphenol is applied in the form of a liquid.

7. The method of treating tinea as claimed in claim 4, wherein the tea polyphenol is applied in the form of an ointment.

8. The method of treating tinea as claimed in claim 5, wherein the tea polyphenol is applied in the form of a liquid or an ointment and the tinea is tinea pedis, tinea capititis, tinea corpis, tinea cruris, tinea manis, tinea unguium or tinea scrotis.

9. The method of treating tinea as claimed in claim 8, wherein the tea polyphenol is selected from the group consisting of (−)epicatechin, (−)epigallocatechin, (−)epicatechingallate, (−)epigallocatechingallate, free theaflavin, theaflavin monogallate A, theaflavin monogallate B and theaflavin digallate.

10. The method of treating tinea as claimed in claim 9, wherein the tinea fungus is *Trichophyton menagrophytes* TIMM 1188 strain.

11. The method of treating tinea as claimed in claim 9, wherein the tinea fungus is *Trichophyton rubrum* TIMM 1216 strain.

12. The method of treating tineas as claimed in claim 10, wherein the tea polyphenol is epigallocatechin gallate.

13. The method of treating tinea as claimed in claim 10, wherein the tea polyphenol is theaflavin digallate.

14. The method of treating tinea as claimed in claim 11, wherein the tea polyphenol is epigallocatechin gallate.

15. The method of treating tinea as claimed in claim 11, wherein the tea polyphenol is theaflavin digallate.

* * * * *